United States Patent [19]
Gusakov

[11] Patent Number: 5,140,309
[45] Date of Patent: Aug. 18, 1992

[54] BED SIGNALLING APPARATUS

[75] Inventor: Ignaty Gusakov, East Aurora, N.Y.

[73] Assignee: Gaymar Industries, Inc., Orchard Park, N.Y.

[21] Appl. No.: 668,062

[22] Filed: Mar. 12, 1991

[51] Int. Cl.5 .............................. G08B 21/00
[52] U.S. Cl. ........................ 340/573; 340/666
[58] Field of Search ......................... 340/573, 666

[56]  References Cited

U.S. PATENT DOCUMENTS

| | | | |
|---|---|---|---|
| 3,439,358 | 4/1969 | Salmons | 340/552 |
| 3,533,095 | 10/1970 | Collins | 340/573 |
| 3,781,843 | 12/1973 | Harrison et al. | 340/573 |
| 3,822,425 | 7/1974 | Scales | 5/456 |
| 4,020,482 | 4/1977 | Feldl | 340/573 |
| 4,068,870 | 1/1978 | Whitney et al. | 285/320 |
| 4,175,263 | 11/1979 | Triplett et al. | 340/573 |
| 4,216,469 | 8/1980 | Hirmann et al. | 340/666 |
| 4,228,426 | 10/1980 | Roberts | 340/573 |
| 4,242,672 | 12/1980 | Gault | 340/573 |
| 4,337,726 | 7/1982 | Czekajewski et al. | 119/15 |
| 4,391,009 | 7/1983 | Schild et al. | 5/453 |
| 4,454,615 | 6/1984 | Whitney | 5/449 |
| 4,483,030 | 11/1984 | Flick et al. | 5/458 |
| 4,633,237 | 12/1986 | Tucknott et al. | 340/573 |
| 4,638,307 | 1/1987 | Swartout | 340/666 |
| 4,700,180 | 10/1987 | Vance | 340/573 |
| 4,899,133 | 2/1990 | Bartlett | 340/573 |
| 4,907,845 | 3/1990 | Wood | 340/573 |
| 4,935,968 | 6/1990 | Hunt et al. | 5/453 |

Primary Examiner—Glen R. Swann, III
Attorney, Agent, or Firm—Young & Thompson

[57]  ABSTRACT

A bed signalling apparatus signals a caregiver an out of bed condition and a bottoming condition of a patient. Signalling of patient location within a bed is also provided. The bed signalling apparatus includes a fluid supplying member connected to at least one resilient member to supply fluid under pressure thereto, such fluid flowing from an inlet of the resilient member to an outlet of the resilient member. At least one switching member is connected between the resilient member and the fluid supplying member for controlling at least one indicating member attached to the switching member in response to changes in pressure within the resilient member.

33 Claims, 3 Drawing Sheets

BED SIGNALLING APPARATUS

BACKGROUND OF THE INVENTION

1. Field of the Invention

The present invention relates to a sensor for use in signalling when a patient falls out of or otherwise leaves a bed against the wishes of a caregiver. The sensor is also useful in signalling when a patient who is lying on a mattress overlay product such as foam or an air cushion contacts the mattress surface underneath the overlay product.

2. Description of the Prior Art

There is a need for effective signalling of a caregiver when a patient, who is likely to suffer injury by leaving his bed without assistance, falls or gets out of bed. There is also a need for effective signalling of a caregiver when a patient, who is lying upon a mattress overlay to reduce tissue interface pressure and in turn prevent or treat pressure ulcers, bottoms upon the mattress; that is, when part of the patient such as a bony prominence, contacts the mattress surface beneath the overlay product.

Various patient monitors are known in the prior art. For example, U.S. Pat. No. 4,020,482 to Feldl relates to a patient monitor including an elongated air inflated flexible bag placed below a mattress and connected to a pressure actuated electrical switch at a remote station. The switch is a normally closed low pressure switch which remains open as long as a patient's weight is on the mattress and closes when the patient's weight is removed. In essence, removal of the weight lowers the pressure in the bag which closes the switch. U.S. Pat. No. 3,533,095 to Collins is of interest in that an air mattress is provided upon which an animal is placed in a first position. For example, a mare is placed upon the mattress in a standing position. When the mare lies down the displacement of her weight causes air from the mattress to expand into a connection to a normally open pressure switch, thereby closing the switch and activating an alarm.

U.S. Pat. No. 3,781,843 to Harrison et al. is of interest in that pressurized fluid is contained in members having a fluid filled passageway which can be attached to the side rails, etc. of a bed. When someone gets out of the bed he typically will grasp such rails and activate an alarm. U.S. Pat. No. 4,175,263 to Triplett et al. is of interest in that it relates to a plurality of pressure sensors.

U.S. patents of general interest which relate to electrical switches which are directly activated by contacts which close under the weight of a patient and open when such weight is removed include the following:

| | |
|---|---|
| 4,228,426 | Roberts |
| 4,242,672 | Gault |
| 4,638,307 | Swartout |
| 4,700,180 | Vance |

The use of a sensor relying upon a fluid such as air under pressure is highly desirable. However, known sensors of this type are subject to leakage or rupture of a sealed bladder. It is an object of the present invention to provide a sensor which is responsive to changes in the fluid pressure of a constantly supplied fluid to signal an out of bed condition or a bottoming condition or both but which is not prone to leakage or rupture.

It is also an object of the present invention to provide such a sensor which will allow the use of multiple resilient means having a fluid continuously supplied under pressure thereto.

Another object of the present invention is to provide such a sensor which will allow a caregiver at a remote location to readily determine whether a patient is in or out of a bed.

A further object of the present invention is to provide such a sensor which will allow a caregiver at a remote location to readily determine whether a patient has bottomed when lying on a mattress overlay device.

Yet another object of the present invention is to provide such a sensor which will allow a caregiver at a remote location to readily determine the position of a patient relative to the surface upon which the patient is lying.

SUMMARY OF THE INVENTION

This invention achieves these and other results by providing a sensor which comprises resilient means through which fluid under pressure can flow from an inlet for the resilient means through an open outlet for the resilient means. Fluid supplying means is connected to the inlet for continuously supplying fluid under pressure toward the resilient means. Switching means is connected between the resilient means and the fluid supplying means for controlling an indicating means in response to changes in the pressure. Indicating means is connected to the switching means for indicating when there has been a change in pressure. The sensor of the present invention is useful in those instances where air flow under the patient will not be detrimental to the patient such as might be the case when a patient is undergoing treatment. A version is shown wherein the air is returned to the pump or away from the patient in those cases where this feature is needed.

BRIEF DESCRIPTION OF THE DRAWINGS

This invention can be clearly understood by reference to the attached drawings in which.

DESCRIPTION OF THE PREFERRED EMBODIMENT

Figure 1:
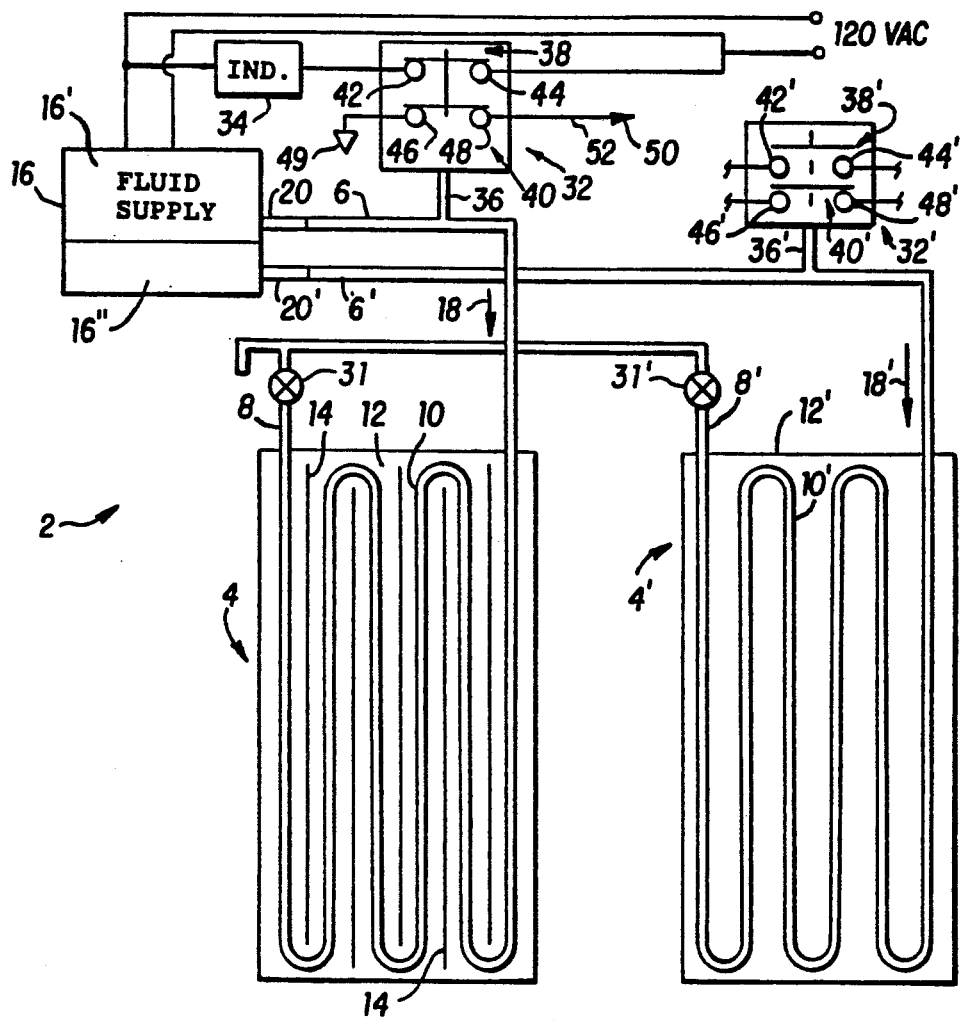
FIG. 1 is a diagrammatic representation of one embodiment of the sensor of the present invention.

The embodiment of this invention which is illustrated in FIG. 1 is particularly suited for achieving the objects of this invention. FIG. 1 depicts a sensor 2 which includes a resilient means 4 through which fluid under pressure can flow from an inlet 6 for the resilient means 4 through an open outlet 8 for the resilient means 4. The resilient means 4 can be in the form of a tube, cell or other form of fluid passage 10 adapted to allow fluid such as air to flow from the inlet 6 through the outlet 8 when the passage 10 is not collapsed by the weight of a patient as described herein. In one embodiment, the passage 10 is in the form of a tube attached to or made integral with a thin and flexible plastic base 12 by means of heat sealing, gluing and the like. In a preferred embodiment, the passage 10 is formed by heat sealing or welding together two or more layers of plastic film. Heat sealing or welding together layers of plastic film is described in U.S. Pat. No. 4,483,030 to Flick et al. which is assigned to Medisearch PR, Inc., a wholly owned subsidiary of the same assignee as this invention, Gaymar Industries, Inc. In the preferred embodiment, the resilient means 4 includes at least one fluid passage 10 which is oriented in a serpentine manner in the plane of base 12 as depicted in FIG. 1. In the embodiment of FIG. 1, the passage 10 includes a serpentine pattern which includes five turns. More or less turns can be provided if desired. In some applications such as when the resilient means 4 is to be positioned on top of a tissue pressure relieving pad or cushion, undesirable shear forces and hammocking between the patient and the resilient means 4 can be reduced by providing slits 14 which extend through the base 12 and are located between the various serpentine loops of the fluid passage 10.

A fluid supplying means 16 is connected to the inlet 6 for continuously supplying fluid under pressure toward the resilient means 4 in the direction of arrow 18. When the passage 10 is not collapsed by the weight of a patient as described herein, fluid under pressure will be caused to flow from the fluid supplying means 16 and through inlet 6, passage 10, and open outlet 8. In the preferred embodiment, the fluid supplying means 16 includes a pump having a pump outlet 20 connected for pumping fluid such as air to inlet 6. As depicted in such preferred embodiment, the open outlet 8 is vented directly to the atmosphere. Alternatively as partially depicted in FIG. 1A, the pump can also include a pump inlet 22, and the open outlet 8 of the resilient means 4 can be connected to such pump inlet at 24 rather than being vented directly to the atmosphere. In such alternate embodiment the pump inlet 22 includes a first end 26 connected to the pump and an opposite second end 28 vented to the atmosphere, the open outlet 8 being connected to the pump inlet 22 between ends 26 and 28. If desired, the pump inlet 22 can be vented to the atmosphere through a restriction or orifice 30 which is positioned between end 28 and open outlet 8. An example of such an orifice is a flat plate or disc having an aperture therethrough the dimensions of which will depend upon the degree to which it is desired to restrict the loss of air from the system at the position of the orifice. Such an orifice is known in the art. In this manner, inlet air can be provided to the pump from the atmosphere at end 28 through orifice 30 and from the open outlet 8. This will result in a larger pressure drop across the resilient means 4 providing more efficient performance than when the air supplied by pump 16 through the resilient means 4 is exhausted directly to the atmosphere as described herein with respect to the embodiment of FIG. 2. The orifice 30 permits maintaining a supply of make-up air as well as compensating for atmospheric pressure changes. The orifice 30 allows the return air from the resilient means that is connected to the pump inlet to fall below atmospheric pressure if the resilient means is occluded or restricted. This results in a larger pressure drop across the resilient means than would exist if it were simply exhausted to atmosphere. The orifice restriction to atmosphere also allows air from atmosphere to enter the system if the otherwise closed system requires it such as when barometric pressure changes, temperature changes, air leaks from the pump or the sensor flow demand changes. Use of the orifice 30 is optional. In the preferred embodiment, the exhaust air will vent directly to atmosphere as described above. If desired, an orifice 31 can be provided similar to orifice 30 but located in the conduit which forms the open outlet 8 as depicted in FIG. 1. In particular, orifice 31 will create back pressure in the sensor the degree of which will depend upon the weight of the patient.

Switching means 32 is connected between the resilient means 4 and the fluid supplying means 16 for controlling indicating means 34 in response to changes in pressure in the fluid supplied by the fluid supplying means, as described herein. Indicating means 34 indicates when there has been a change in such pressure. In the embodiment of FIG. 1, the switching means 32 is connected to the inlet 6 through a conduit 36 such that the fluid supplying means or pump 16 can pump air under pressure to the resilient means 4 and to the switching means 32. Switching means 32 includes normally closed contacts. In the embodiment of FIG. 1, the switching means includes a plurality of contact means 38, 40 each of which is electrically connected to a respective indicating means. For example, contact means 38 includes normally closed contacts 42, 44 which are electrically connected to indicating means 34. Indicating means 34 can be in the form of, for example, an audio and/or visual alarm. In a like manner, contact means 40 includes normally closed contacts 46, 48 which are electrically connected to an indicating means by connecting the signal line to the nurse's call at a nurse's station to its signal common 49. Although the nurse's call is not shown, arrow 50 is representative of line 52 extending to such an indicating means. The switching means 32 can be in the form of, for example, a pressure switch or other pressure sensing device such as a transducer. In the embodiment of FIG. 1, the switching means is in the form of a pressure switch with normally closed contacts.

In operation, the pump 16 provides low pressure air to the resilient means through inlet 6 and air passage 10 and to the switching means 32 through conduit 36. The weight of a patient lying on the resilient means 4 will cause the passage 10 of the resilient means 4 to collapse thereby preventing air flow to continue through passage 10. This causes the pressure at the outlet 20 of the pump to increase. Such increase in pressure is sensed by the pressure switch of switching means 32 causing the normally closed contacts 42, 44 and 46, 48 to open thereby deactivating the indicating means. If the patient were to get up or otherwise leave the bed, the collapsed passage 10 of the resilient means 4 would rebound to its original open configuration allowing air to continue to flow therethrough and to exit at the open outlet 8. Such freely flowing air will cause the pressure at the outlet 20 of the pump to decrease with a corresponding decrease in the air pressure in the switching means 32 causing contacts 42, 44 and 46, 48 to close. Closure of such contacts will activate the alarm at indicating means 34 and the nurse's call connected to line 52, respectively.

Without limitation, the resilient means 4 is of the type which can be positioned directly beneath or on top of a bed mattress, or if desired between the mattress and a tissue pressure relieving bed pad or cushion such as a foam pad, or an air cushion as is described in U.S. Pat.

No. 4,483,030, referred to above, or U.S. Pat. No. 4,454,615 to Whitney which is assigned to Medisearch PR, Inc. to provide signalling means to a caregiver when a patient is out of the bed. In an alternate embodiment, a similar resilient means can be positioned between the bed mattress and an overlay pressure relieving cushion to serve as a bottoming sensor to provide signalling means to the caregiver if the overlay becomes compressed between the patient and the mattress to the extent to cause the patient to feel the presence of the mattress. For example, if the overlay is an air cushion of the type described in U.S. Pat. Nos. 4,483,030 or 4,454,615 which might lose air by leakage or in some other manner, or a foam cushion which does not provide satisfactory patient support, then the patient will "bottom" causing the patient to feel the presence of the mattress and to lose the benefit of the overlay. A resilient means 4' can be provided to signal the caregiver in the event that such bottoming occurs. Except as noted herein, the sensor 2 with resilient means 4' functions in the same manner as with resilient means 4, and like reference numerals have been used with a prime designation to designate similar parts. Sensor 4' does not include slits 14 although such slits can be provided if desired. The primary difference in using the resilient means 4' as a bottoming sensor is that the switching means 32' includes normally open contacts. In the embodiment of FIG. 1, the switching means includes a plurality of contact means 38', 40' each of which is electrically connected to a respective indicating means (not shown). For example, contact means 38' includes normally open contacts 42' 44' which can be electrically connected to an indicating means in the form of, for example, an audio and/or visual alarm (not shown) in the same manner in which contacts 42, 44 are connected to alarm 34. In a like manner, contact means 40' include normally open contacts 46', 48' which can be electrically connected to a nurse's call at a nurse's station. The switching means 32' can be in the form of, for example, a pressure switch or other pressure sensing device such as a transducer. In the embodiment of FIG. 1, the switching means 32' is in the form of a pressure switch with normally open contacts.

In operation, the pump 16 provides low pressure air to the resilient means 4' through inlet 6' and air passage 10' and to the switching means 32' through conduit 36'. A patient lying upon an overlay such as an air pad positioned on top of the resilient means 4' will not engage the resilient means 4' if there is sufficient air in the pad. Since the patient will not be engaging the resilient means 4', the air will be free to flow through the passage 10' as long as sufficient pressure is provided by pump 16 and to exit at the open outlet 8'. In such a mode, the air pressure at the outlet 20' of the pump will be low and will not overcome the normally open position of the contacts 42', 44' and 46', 48' and therefore the indicating means will not be activated. Should the overlay air pad become deflated to the point where the patient bottoms, the weight of the patient bearing against resilient means 4' will cause the passage 10' to collapse thereby preventing air flow to continue through passage 10'. This causes the pressure at the outlet 20' of the pump to increase. Such increase in pressure is sensed by the pressure switch of switching means 32' causing the normally open contacts 42', 44' and 46', 48' to close. Closure of such contacts will activate the alarm and nurse's call (not shown), respectively. If desired, an orifice 31' similar to orifice 31 can be provided.

If desired, the sensor 2 can include at least one switching means which includes normally open contacts and at least another switching means which includes normally closed contacts. For example, in the preferred embodiment of FIG. 1, the sensor 2 includes the resilient means 4 for use in sensing when a patient leaves a bed and the resilient means 4' for use in sensing bottoming of the patient. As described herein, resilient means 4 functions in combination with normally closed contacts 42, 44 and 46, 48 and resilient means 4' functions in combination with normally open contacts 42', 44' and 46', 48'. In such embodiment, the fluid supplying means is in the form of pump 16 having two fluid supply outlets 20 and 20' which function independently of each other, fluid supply outlet 20 supplying fluid to control activation of the normally closed contacts and fluid supply outlet 20' supplying fluid to control activation of the normally open contacts. Outlets 20 and 20' can be caused to function independently by having each associated with a separate pump 16', 16" as depicted in FIG. 1. Alternatively, and without limitation, a single pump can be used with an orifice or pressure relief valve or the like being provided in the line 20 and another orifice or pressure relief valve or the like being provided in line 20'.

Figure 2:
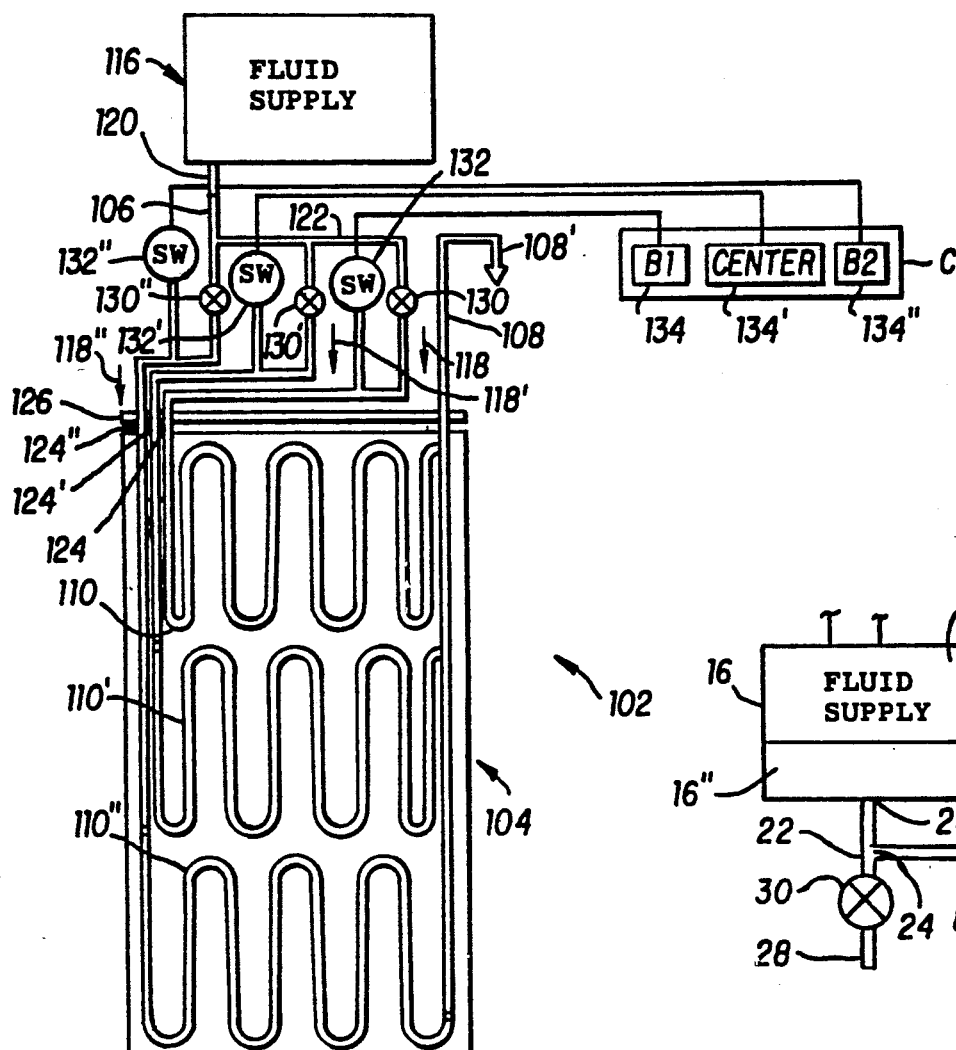
FIG. 2 is a diagrammatic representation of another embodiment of the sensor of the present invention.

In an alternate embodiment depicted in FIG. 2, a sensor 102 is provided which includes a resilient means 104 through which fluid under pressure can flow from an inlet 106 for the resilient means 104 through an open outlet 108 for the resilient means 104. The resilient means 104 can be fabricated as described above regarding resilient means 4. However, resilient means 104 includes a plurality of tubes, cells or other fluid passages 110, 110', 110" adapted to allow fluid such as air to flow from inlet 106 through the outlet 108 with respect to those fluid passages 110, 110', 110" which are not collapsed by the weight of a patient as described herein. It is preferred that fluid passages 110' and 110" be non-collapsible where they extend upon the resilient means 104 adjacent to fluid passage 110, and that fluid passage 110" also be non-collapsible where it extends upon the resilient means 104 adjacent fluid passage 110'. In a like manner it is preferred that the outlet 108 be non-collapsible at least where it extends upon the resilient means 104 from its connection to fluid passage 110 to its connection to fluid passage 110".

Figure 1A:
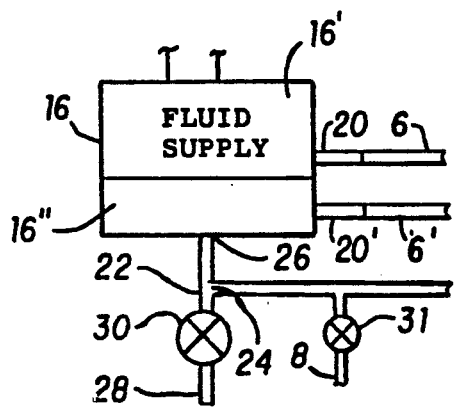
FIG. 1A is a partial diagrammatic representation of an alternative embodiment of the present invention.

A fluid supplying means 116 such as a pump is connected at pump outlet 120 to the inlet 106 for continuously supplying fluid under pressure toward the resilient means 104 in the direction of arrows 118, 118', 118". To this end, inlet 106 is connected to a manifold 122. Each fluid passage 110, 110', 110" includes a respective fluid passage inlet 124, 124', 124" which is connected to manifold 122. Inlets 124, 124', 124" can be connected directly to manifold 122 or, as depicted in FIG. 2, can be connected to the manifold through a pneumatic connector 126. An example of such a pneumatic connector is described in U.S. Pat. No. 4,068,870 to Whitney and assigned to the assignee of the present invention, Gaymar Industries, Inc. A plurality of switching means 132, 132', 132" similar to switching means 32 of FIG. 1 is provided, each switching means being connected between the fluid supplying means 116 and a respective fluid passage 110, 110', 110" as depicted in FIG. 2. A plurality of indicating means diagrammatically represented at 134, 134', 134" is provided, each indicating means being connected to a respective switching means. In the embodiment of FIG. 2, each switching means 132, 132', 132" can include normally open contacts (not shown), the contacts in each switching means being electrically connected to a respective indicating means 134, 134', 134". Orifices 130, 130', 130" similar to orifice 30 of FIG. 1A are connected between the fluid supplying means 116 and a respective switching means 132, 132', 132".

In operation, the sensor of FIG. 2 includes a plurality of fluid passages 10, 110', 110" which operate independently as far as the patient load is concerned. FIG. 2 depicts three fluid passages 110, 110', 110". However, more or less fluid passages can be used as desired. This feature allows the detection of movement of a patient as, for example, when the patient is getting close to an edge of the bed.

Figure 3:
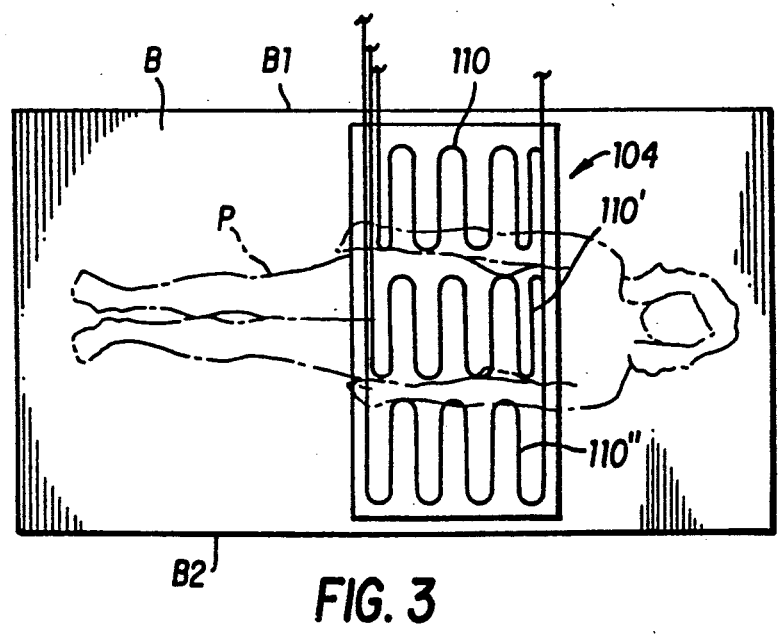
FIG. 3 is a diagrammatic representation of the embodiment of FIG. 2 in use.

To understand the embodiment of FIG. 2, reference is also made to FIG. 3 which depicts a bed B, resilient means 104 and patient P. Prior to when the patient is placed upon the resilient means 104, air supplied at low pressure by fluid supplying means 116 will be free to flow through inlet 106, manifold 122, inlets 124, 124', 124" and passages 110, 110', 110" and to exit at the common open outlet 108 to be vented directly to atmosphere at 108'. Such atmospheric exhaust air is preferably directed away from the patient by locating the end 108' off of the bed or near the pump. In such a mode, the air pressure sensed at each switching means will be low and will not overcome the normally open position of the contacts in each respective switching means 132, 132', 132". Therefore, in such mode none of the indicating means 134, 134', 134" will be activated. When a patient P is positioned in the bed B, the patient will typically be placed in the middle of the bed as depicted in FIG. 3 such that the weight of the patient will bear against the passage 110' causing passage 110' to collapse thereby preventing air flow to continue through passage 110'. This causes an increase in pressure to be sensed by the switching means 132' thereby causing the normally open contacts in switching means 132' to close. Such an increase in pressure is facilitated by the presence of the orifice 130'. Closure of such contacts will activate the indicating means 134' which can include a lamp positioned in the middle of a control panel C designating that the patient is in the middle of the bed B. Air will continue to flow through passages 110, 110" thereby maintaining at a relatively low level the air pressure sensed by switching means 132, 132", the normally open contacts in switching means 132, 132" continuing to be at their normally open position. Should the patient move toward edge B1 of the bed, the patient will collapse passage 110 causing an increase in pressure to be sensed by the switching means 132 thereby causing the normally open contacts in switching means 132 to close. Such an increase in pressure will be facilitated by the presence of the orifice 130. Closure of such contacts will activate the indicating means 134 which can include a lamp positioned in the left-hand side of control panel C designating that the patient has moved toward edge B1. If the patient continues to move toward edge B1 he will roll off of collapsed passage 110' configuration allowing air to once again flow therethrough and to exit at the open outlet 108. The freely flowing air will cause the pressure sensed by switching means 132' to decrease causing the normally open contacts of switching means 132' to open thereby deactivating the lamp at indicating means 134'. The lamp at 134 will continue to be activated indicating that the patient has moved further from the center of the bed. It will be apparent to those skilled in the art that by providing more independent fluid passages, switching means and indicating means, a more precise determination of patient location within the bed can be obtained. It will also be apparent to those skilled in the art that movement toward edge B2 will activate a lamp at indicating means 134" which can be positioned at the right-hand side of control panel C designating that the patient has moved toward edge B2.

If desired, the fluid supplying means of the present invention can be the same pump used to inflate an air cushion-type overlay such as is manufactured by Gaymar Industries under Model Numbers APP30, APP50, AFP255 and AFP355.

In the various embodiments described herein it often will be desirable to provide means associated with the switching means to reduce inadvertent activating of the indicating means as a result of normal patient movements. This is particularly true in those embodiments designed to activate the indicating means when the patient is out of the bed. In such instances, it might be desirable to provide a time delay.

Figure 4:
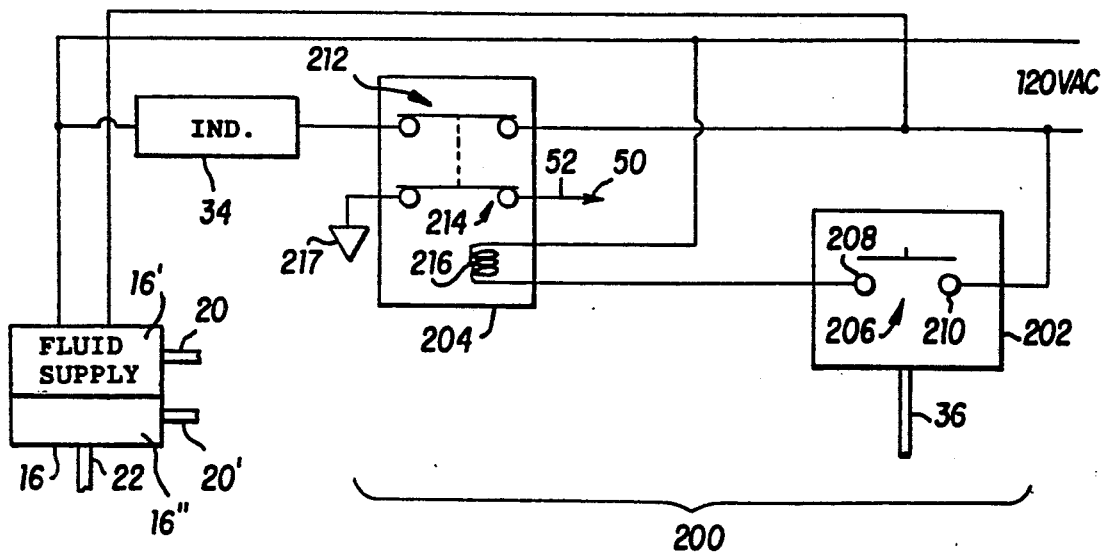
FIG. 4 is a diagrammatic representation of yet another embodiment of the sensor of the present invention.

FIG. 4 depicts a modification of the switching means 32 of FIG. 1. In such modification, the switching means 32 is replaced by a switching means 200 which includes a pressure switch 202, coupled to the fluid supplying means 16 by conduit 36, and a time delay relay 204. The use of a time delay will prevent nuisance activating of the indicating means and will allow resetting of the sensor when the patient is removed from the bed. Pressure switch 202 includes contact means 206 which includes normally open contacts 208, 210. An example of a time delay 204 which can be used in the present invention is, without limitation, type CWD-38-66000 sold by Potter Brumfield. For purposes of simplification of the drawing, the circuitry of time delay relay 204 is not depicted except for the normally closed contact means 212 and 214 and the relay coil 216.

In operation, when the patient is no longer on the resilient means 4, air will freely flow through the passage 10 as described herein and the pressure switch 202 will be deactivated and the normally open contact means 206 will be open. Since the circuit of coil 216 is connected in series with the pressure switch 202 and thereby to the source of voltage, which is depicted by way of example as 120 VAC, the relay coil 216 will be de-energized, by virtue of the open contacts 208, 210 and the time delay relay will deactivate. If the duration of the patient being off of the sensor is longer than the predetermined delay, the normally closed relay contact means 212 and 214 will be closed completing the circuit to the indicating means 34 and the nurse's call. As depicted in FIG. 4, contact means 212 will connect the 120 VAC to the alarm at 34 and the other contact means 214 will connect the nurse's call signal line to its circuit common 217 to alert the attending clinicians. When the patient returns to the resilient means 4, air pressure will increase in the pressure switch 202 causing the contacts 208, 210 of the contact means 206 to close and the time delay relay coil 216 to be energized. After the preset delay time elapses, the normally closed relay contact means 212 and 214 will open thereby deactivating the indicating means 34 and the nurse's call. It should be noted that the time delay can be set at zero or the delay circuit can be bypassed or eliminated if no delay is desired In the preferred embodiment, inadvertent activation of the indicating means can also be minimized by providing non-collapsible conduits except in the region of the fluid passages such as at 10, 10' and 110, 110', 110" which are intended to be collapsed by the weight of the patient as described herein. For example, as noted herein the passages 110', 110" and the outlet 108 are provided with lengths which are non-collapsible.

Figure 5:
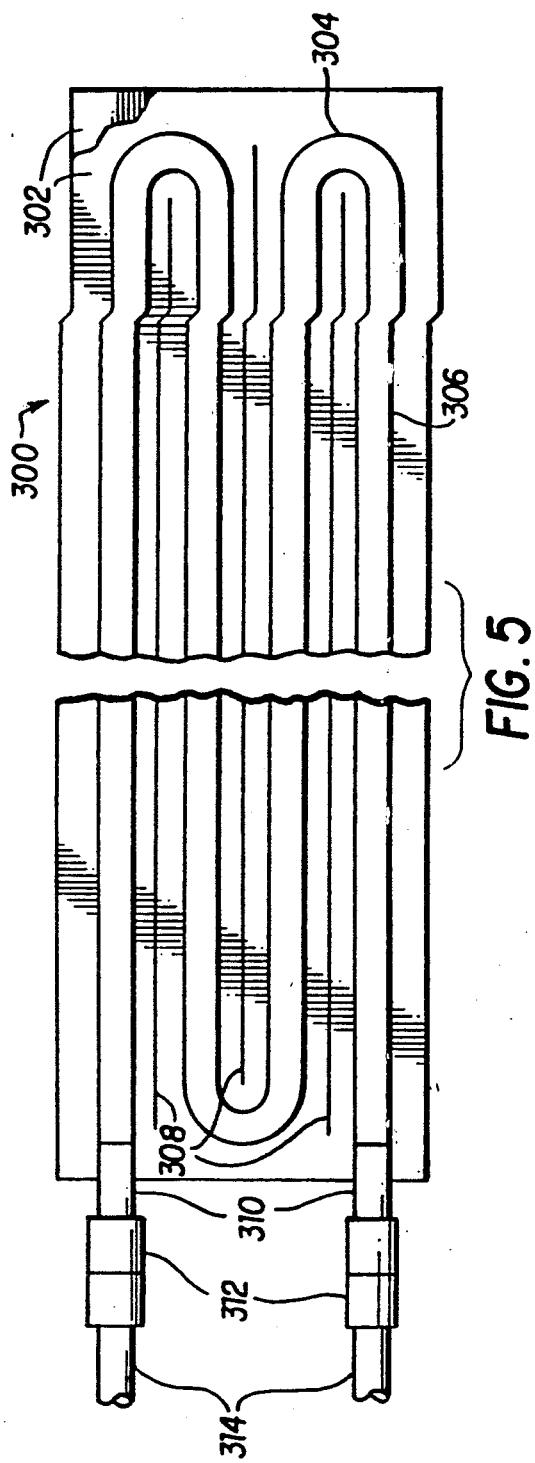
FIG. 5 is a diagrammatic representation of another embodiment of the sensor of the present invention.
Figure 6:
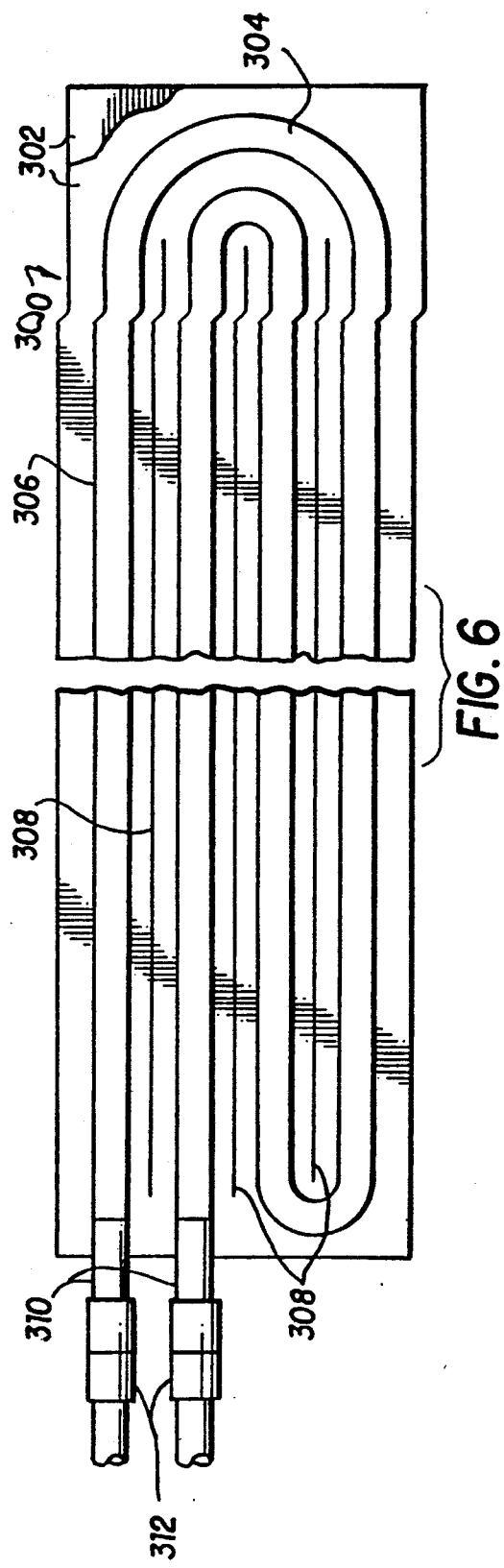
FIG. 6 is a diagrammatic representation of another embodiment of the sensor of the present invention.

FIGS. 5 and 6 depict two different flow patterns of a sensor 300 of the present invention. Both versions are made of two layers of plastic film 302 heat sealed to create the sensor flow passages 304. The film material can be polyvinyl chloride, polyurethane, polyethylene, nylon or other suitable thin flexible material. Heat seals 306 are created adjacent to the flow passages 304. Slits 308 are optional but when used allow unrestricted movement of the sensor 300 in the plane of the sensor so that shear forces on the patient are reduced. Plastic hose or tubing 310 made of material that is similar to that of the film 302 is heat sealed into the sensor air passage 304 in order to make pneumatic connection to the sensor 300. Pneumatic connectors 312 are inserted or connected to the tubing 310 and the tubes 314 that connect to the pump. An example of such pneumatic connectors is described in U.S. Pat. No. 4,068,870.

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

I claim:

1. A sensor, comprising:
   resilient means through which fluid under pressure can flow from an inlet for said resilient means to an outlet for said resilient means;
   fluid supplying means connected to said inlet for continuously supplying fluid under pressure toward said resilient means;
   switching means connected between said resilient means and said fluid supplying means for controlling indicating means in response to changes in said pressure; and
   indicating means connected to said switching means for indicating when there has been a change in said pressure.

2. The sensor of claim 1 wherein said open outlet of said resilient means is vented to atmosphere.

3. The sensor of claim 2 wherein said fluid supplying means includes a pump having a pump outlet connected for pumping air to said inlet for said resilient means and to said switching means.

4. The sensor of claim 3 wherein said pump includes a pump inlet having a first end connected to said pump and an opposite second end vented to atmosphere.

5. The sensor of claim 4 further including an orifice positioned between said first end and said opposite second end.

6. The sensor of claim 3 wherein said switching means includes means for reducing inadvertent activation of said indicating means.

7. The sensor of claim 2 wherein said outlet includes an orifice.

8. The sensor of claim 1 wherein said fluid supplying means includes a pump having a pump outlet connected for pumping air to said inlet for said resilient means and to said switching means.

9. The sensor of claim 8 wherein said pump includes a pump inlet and further wherein said outlet of said resilient means is connected to said pump inlet.

10. The sensor of claim 9 wherein said pump inlet includes a first end connected to said pump and an opposite second end vented to atmosphere, said outlet for said resilient means being connected to said pump inlet between said first end and said opposite second end.

11. The sensor of claim 10 further including an orifice positioned between said opposite second end and said outlet for said resilient means.

12. The sensor of claim 9 wherein said switching means includes means for reducing inadvertent activation of said indicating means.

13. The sensor of claim 1 wherein said switching means includes normally closed contacts.

14. The sensor of claim 1 wherein said switching means includes normally open contacts.

15. The sensor of claim 1 wherein said switching means includes a plurality of contact means each of which is electrically connected to a respective indicating means.

16. The sensor of claim 15 wherein each contact means includes normally open contacts.

17. The sensor of claim 15 wherein each contact means includes normally closed contacts.

18. The sensor of claim 15 wherein at least one of said contact means includes normally open contacts and further wherein at least another of said contact means includes normally closed contacts.

19. The sensor of claim 18 wherein said switching means includes means for reducing inadvertent activation of said indicating means.

20. The sensor of claim 1 wherein said fluid supplying means includes a plurality of fluid supply outlets and further wherein said resilient means includes a plurality of resilient means each of which includes a respective inlet and a respective open outlet, each fluid supply outlet being connected to a respective inlet.

21. The sensor of claim 20 further including a plurality of switching means, each switching means of said plurality of switching means being connected between a respective fluid supply outlet and a respective inlet.

22. The sensor of claim 21 further including a plurality of indicating means, each indicating means of said plurality of indicating means being connected to a respective switching means.

23. The sensor of claim 22 wherein at least one of said switching means includes normally open contacts and further wherein at least one other of said switching means includes normally closed contacts.

24. The sensor of claim 22 wherein said fluid supply outlets include at least one fluid supply outlet which functions independently of at least one other fluid supply outlet.

25. The sensor of claim 24 wherein said at least one fluid supply outlet supplies fluid to control activation of a switching means having normally closed contacts and at least one other of said fluid supply outlets supplies fluid to control activation of a switching means having normally open contacts.

26. The sensor of claim 22 wherein said switching means includes means for reducing inadvertent activation of said indicating means.

27. The sensor of claim 20 wherein each respective outlet includes an orifice.

28. The sensor of claim 1 wherein said resilient means includes at least one serpentine oriented fluid passage.

29. The sensor of claim 1 wherein said resilient means includes a base and at least one fluid passage which is oriented in a serpentine manner in the plane of said base, and further including slits which extend through said base and are positioned between loops which form said orientation in a serpentine manner.

30. The sensor of claim 1 wherein said resilient means includes a plurality of fluid passages each of which includes a respective fluid passage inlet and a respective fluid passage outlet, said fluid supplying means being connected to each respective fluid passage inlet, further wherein said switching means includes a plurality of switching means each of which is connected between said fluid supplying means and a respective fluid passage, and further wherein said indicating means includes a plurality of indicating means each of which is connected to a respective switching means.

31. The sensor of claim 30 further including a plurality of orifices, each orifice of said plurality of orifices being connected between said fluid supplying means and a respective switching means.

32. The sensor of claim 1 wherein said switching means includes means for reducing inadvertent activation of said indicating means.

33. A sensor, comprising:
an upper surface and a lower surface of plastic film selectively heat sealed together to provide at least one continuous and collapsible fluid flow passage disposed between said upper surface and said lower surface, said at least one fluid flow passage having a fluid inlet and a fluid outlet;
pressure responsive switching means in fluid communication with said at least one fluid flow passage by connection to said fluid inlet for actuating an indicating means in response to changes in pressure within said pressure responsive switching means;
indicating means connected to said fluid responsive switching means for indicating when there has been a change in said pressure; and
fluid supplying means including a pump having a pump outlet connected to said fluid inlet and to said pressure responsive switching means for continuously supplying fluid under pressure to said pressure responsive switching means and said at least one fluid flow passage, said fluid within said pressure responsive switching means being at a first pressure when said at least one fluid flow passage is not collapsed by the weight of a person and being at a second greater pressure when said at least one fluid flow passage is collapsed by the weight of a person.

* * * * *